US00PP24884P2

(12) United States Plant Patent
Huisman

(10) Patent No.: US PP24,884 P2
(45) Date of Patent: Sep. 16, 2014

(54) ***CEANOTHUS* PLANT NAMED 'COOL BLUE'**

(50) Latin Name: *Ceanothus thyriflorus*
Varietal Denomination: Cool Blue

(71) Applicant: Nico Huisman, Boskoop (NL)

(72) Inventor: Nico Huisman, Boskoop (NL)

( * ) Notice: Subject to any disclaimer, the term of this patent is extended or adjusted under 35 U.S.C. 154(b) by 176 days.

(21) Appl. No.: 13/694,200

(22) Filed: Nov. 6, 2012

(51) Int. Cl.
*A01H 5/00* (2006.01)

(52) U.S. Cl.
USPC ..... Plt./226

(58) Field of Classification Search
CPC ..... A01H 5/00
USPC ..... Plt./226
See application file for complete search history.

*Primary Examiner* — June Hwu
(74) *Attorney, Agent, or Firm* — Penny J. Aguirre

(57) ABSTRACT

A new cultivar of *Ceanothus*, 'Cool Blue', characterized by its small variegated leaves with dark green centers and wide creamy white margins, its upright and broadly spreading compact plant habit and its panicles of sweetly fragrant light blue flowers.

2 Drawing Sheets

Botanical classification: *Ceanothus thyriflorus*.
Variety denomination: 'Cool Blue'.

BACKGROUND OF THE INVENTION

The present invention relates to a new and distinct cultivar of *Ceanothu thyriflorus*, and will be referred to hereafter by its cultivar name, 'Cool Blue'. 'Cool Blue' is a new cultivar of evergreen shrub for use as a landscape plant.

The new cultivar of *Ceanothus* was discovered as a naturally occurring branch mutation of *Ceanothus thyrsiflorus* 'Skylark' (not patented) in a container in the Inventor's nursery in 2004 in Boskoop, The Netherlands.

Asexual reproduction of the new cultivar was first accomplished using terminal stem cuttings by the Inventor in Boskoop, The Netherlands in 2004. The characteristics of this cultivar have been determined to be stable and are reproduced true to type in successive generations.

SUMMARY OF THE INVENTION

The following traits have been repeatedly observed and represent the characteristics of the new cultivar as grown outdoors in Boskoop, The Netherlands. These attributes in combination distinguish 'Cool Blue' as a new and unique cultivar of *Ceanothus*.

1. 'Cool Blue' exhibits variegated leaves with dark green centers and wide creamy white margins.
2. 'Cool Blue' exhibits leaves that are small in size.
3. 'Cool Blue' exhibits an upright spreading compact plant habit.
4. 'Cool Blue' produced panicles of sweetly fragrant light blue flowers.

'Skylark', the parent plant, differs from 'Cool Blue' in having larger leaves that are green and non-variegated and in having a more vigorous growth habit. 'Cool Blue' can also be compared to the cultivars of *Ceanothus thysiflorus*; 'Perado' (U.S. Plant Pat. No. 13,433) and 'Born Again' (not patented). 'Perado' differs from 'Cool Blue' in having vareigated foliage with margins that are golden yellow and in having a more vigorous growth habit. 'Born Again' differs most significantly from 'Cool Blue' in having foliage that is mostly golden yellow in color with small blotches of green in the center.

BRIEF DESCRIPTION OF THE DRAWING

The accompanying colored photographs illustrates the overall appearance and distinct characteristics of a 3 year-old plant of the new *Ceanothus* as grown outdoors in a 2-liter container in Boskoop, The Netherlands.

The photograph

Figure 1:
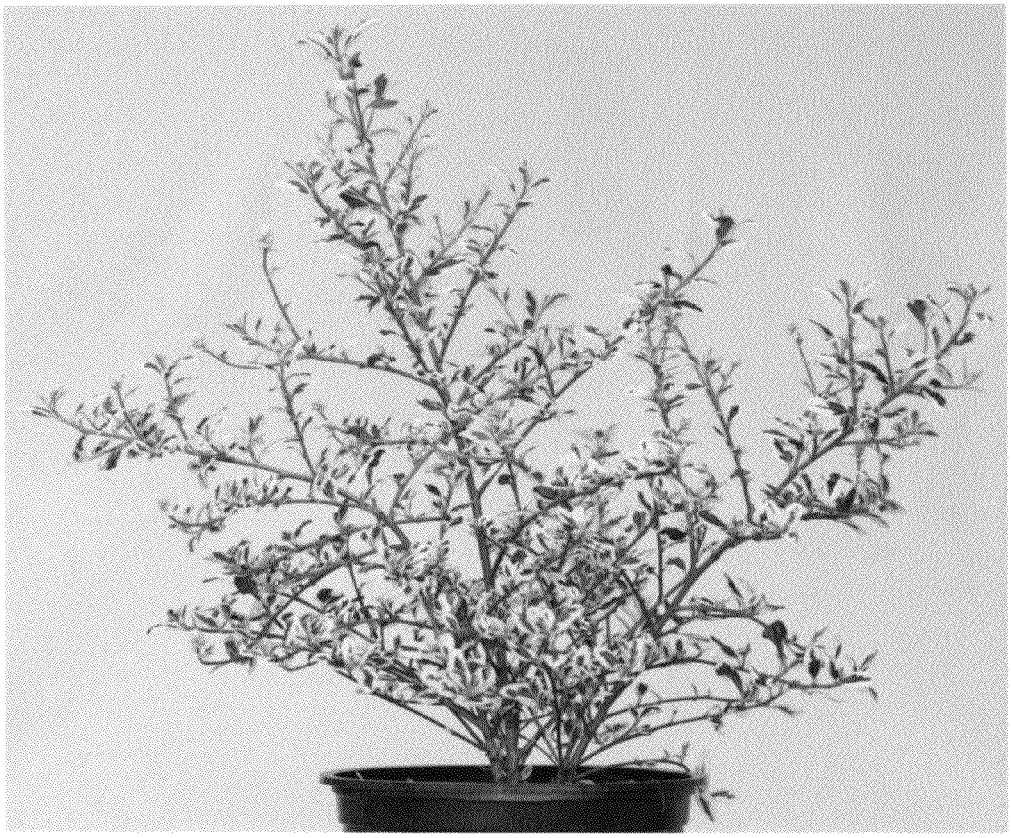
FIG. 1 is a side view and illustrates the overall habit and foliage size of 'Cool Blue'.
Figure 2:
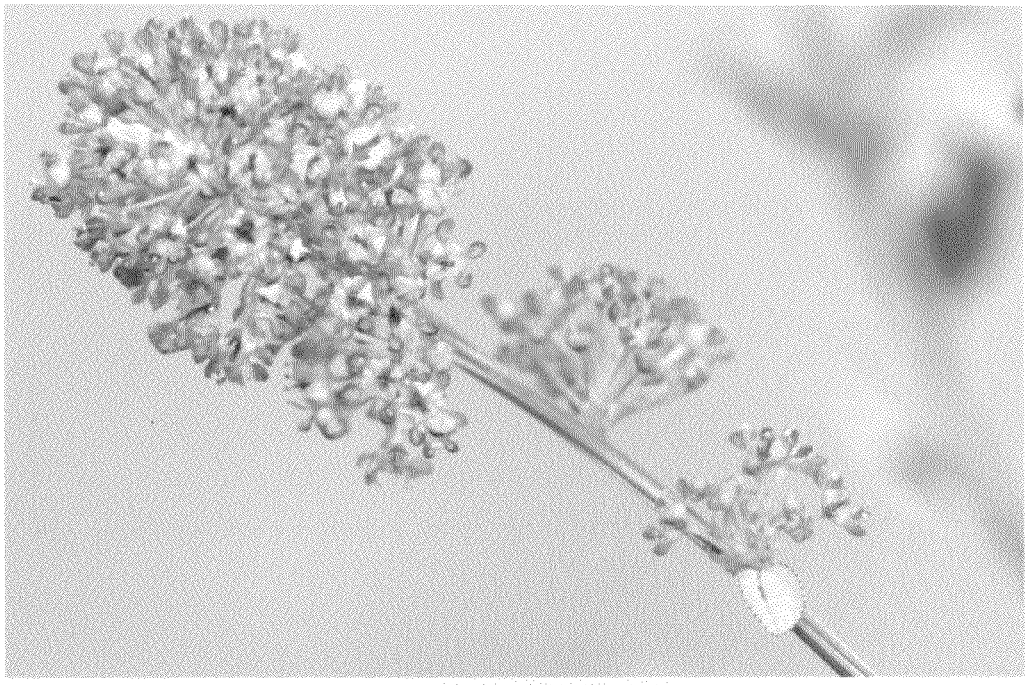

The photograph in FIG. 2 provides a close-up view of an inflorescence of 'Cool Blue'.

Figure 3:
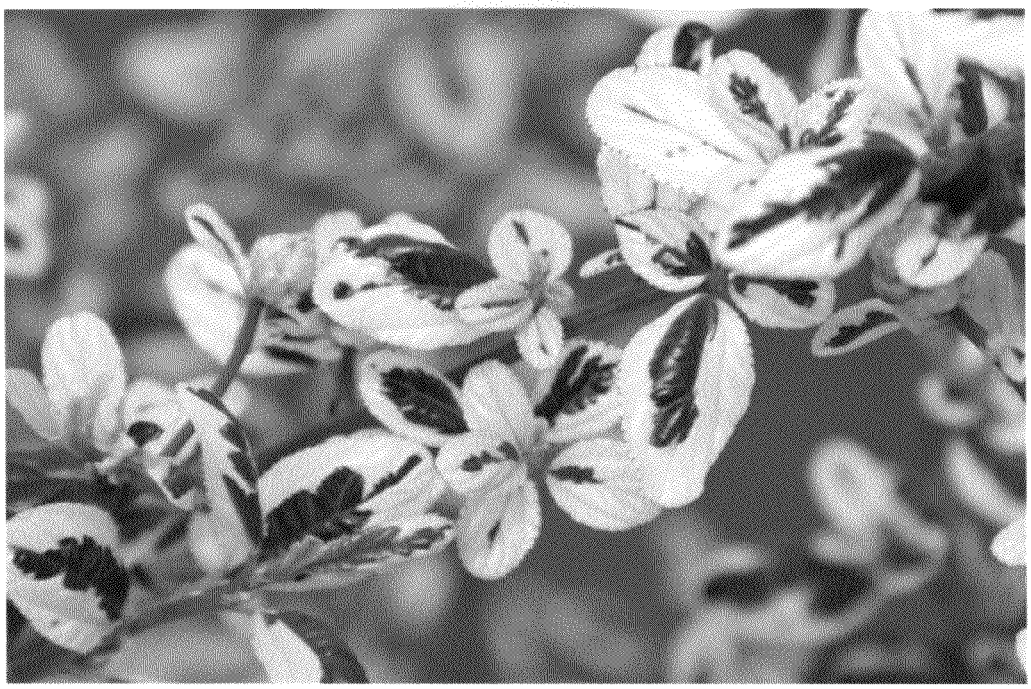

The photograph in FIG. 3 provides a close-up view of the foliage and leaf variegation pattern of 'Cool Blue'. The colors in the photographs may differ slightly from the color values cited in the detailed botanical description, which accurately describe the colors of the new *Ceanothus*.

DETAILED BOTANICAL DESCRIPTION

The following is a detailed description of 3 year-old plants of the new *Ceanothus* as grown outdoors in 2-liter containers in Boskoop, The Netherlands. Plants were grown under average day temperatures of 14° C. to 23° C. and average night temperature of 8° C. to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Evergreen shrub.

*Plant habit*.—Upright, broadly spreading, compact.

*Blooming period*.—May to June with occasional flowers in September to October in Boskoop, The Netherlands.

*Height and spread*.—Average of 36.6 cm in height and 37.4 cm in width as grown in a 2-liter container.

*Cold hardiness*.—At least to U.S.D.A. Zone 7b.

*Diseases and pests*.—Not more susceptable to pests and diseases than other *Ceanothus* varities.

*Root description*.—Fibrous.

*Propagation*.—Terminal stem cuttings.

*Growth rate*.—Moderate.

Stem description:

*Shape*.—Rounded, with 5 indistinct angles.

*Stem color*.—New twigs; between 137B and 143A, mature bark; color between N199A and N200A.

*Stem strength*.—Very strong.

*Stem surface*.—Slightly to moderately glossy and very sparsely covered with short pubescent soft hairs; 0.2 mm in length and to small to be measured with RHS-CC.

*Stem size*.—Main stems; average of 25 cm in length and 3.5 mm in diameter, lateral branches average of 9.7 cm in length and 2.5 mm in diameter, pinching is not required but will improve the number of branches.

*Branching*.—Average of 75 lateral branches and lateral stems an average angle of 55° to main stems.

*Internode length*.—About 1.2 cm.

Foliage description:

*Leaf shape*.—Elliptic to ovate and obovate, moderately convexed.

*Leaf division*.—Simple.

*Leaf base*.—Short attenuate.

*Leaf apex*.—Rounded.

*Leaf fragrance*.—None.

*Leaf venation*.—Pinnate, upper surface; between 147A and N189A, near the margin is between 150D and 157A, lower surface; 147C.

*Leaf margins*.—Revolute, finely serrate.

*Leaf arrangement*.—Alternate.

*Leaf attachment*.—Petiolate.

*Leaf number*.—Average of 9 per lateral branch.

*Leaf surface*.—Upper and lower surface; smooth, green parts are glossy and variegated parts are lightly glossy.

*Leaf size*.—Average of 1.8 cm in length and 1 cm in width.

*Leaf color*.—Young upper surface; N189A, with an irregular margin N144A, young lower surface; 189A with an irregular margin 150B to 150C, mature upper surface; in between 147A and N189A, with an irregular margin between 150D and 157A, mature lower surface; 147B with an irregular margin 150D.

*Petioles*.—Average of 5 mm in length and 1 mm in width, 144B to 144C in color.

*Stipules*.—None observed.

Inflorescence description:

*Inflorescence type*.—Compound axillary and terminal panicles consisting of simple umbels.

*Inflorescence number*.—Average of 140 on a 3-year-old plant.

*Inflorescence size*.—Averages 4.7 cm in height and 2.1 cm in width.

*Flower quantity*.—About 180 per inflorescence.

*Flowering habit*.—Once a year continuously.

*Flowering season*.—Spring (May to June), occasional repeat in autumn (September and October).

*Response time to flower*.—Approximately 8 months.

*Pedicels*.—About 5 mm length and 0.5 mm in diameter, 155C to 157D in color, tinged 108D, moderately strong, held at a 45° angle to peduncle, glabrous surface.

*Peduncle*.—About 3.9 cm in length and 1.5 mm in diameter, average angle of terminal inflorescences is 0° (straight on top of lateral branch), average angle of axillary inflorescences is 45°, moderately strong and 143B in color, glabrous surface.

*Flower buds*.—Flattened globular in shape, 1 mm in length and 2 mm in diameter, between 97A and 98C in color, buds open in approximately 4 days from described stage.

*Flower fragrance*.—Slightly fragrant, sweet and pleasant.

*Persistence of flowers*.—Self-cleaning.

*Lastingness of flowers*.—Flowers last about 1 week.

*Flower type*.—Single.

*Flower aspect*.—Towards all directions.

*Flower shape*.—Rotate.

*Flower size*.—About 5 mm in diameter and 2 mm in depth.

*Petals*.—5, about 2 mm in length and 1 mm in width, petals not fused, spathulate and concave in shape, margin entire, apex obtuse, rotate arrangement, smooth on upper and lower surface, color of newly opening upper and lower surfaces; 94B, color of fully opened upper and lower surfaces; 94B.

*Sepals*.—5, about 2 mm in length and 1 mm in width, lower 30% fused, ovate in shape, margin entire, apex acute, smooth and dull on upper and lower surface, color of immature and mature upper and lower surfaces; ranging between 97D and 100D and 100C.

*Calyx*.—Rotate in shape, about 2 mm in length and 3 mm in diameter.

Reproductive organs:

*Gynoecium*.—1 pistil, about 1 mm in length, stigma cleft (3 parted) and 99B in color, style is about 0.5 mm in length and 99B in color, ovary is 146B in color.

*Androcoecium*.—Average of 5, anthers are basifixed, broadly oval in shape and about 0.3 mm in length, filaments are about 1.75 mm in length and 5D in color, pollen is moderately produced and 5B in color.

*Fruits and seeds*.—No fruit or seed set has been observed.

It is claimed:

1. A new and distinct cultivar of *Ceanothus* plant named 'Cool Blue', as herein illustrated and described.

* * * * *